United States Patent

Dosmann et al.

Patent Number: 5,822,071
Date of Patent: Oct. 13, 1998

[54] SPECTROMETER NORMALIZATION SYSTEM

[75] Inventors: Andrew J. Dosmann, Granger, Ind.; Christine D. Nelson, Edwardsburg, Mich.

[73] Assignee: Bayer Corporation, Elkhart, Ind.

[21] Appl. No.: 826,297

[22] Filed: Mar. 27, 1997

[51] Int. Cl.$^6$ .......................... G01N 21/00; G01N 21/27; G01J 3/28

[52] U.S. Cl. .......................... 356/435; 356/414; 356/326; 250/575

[58] Field of Search .......................... 356/402–411, 323, 356/319, 320, 321, 324, 325, 326, 414–416, 417–420, 436, 51, 39, 432–434, 440–442, 244, 435, 246, 330–334; 422/62–63, 67, 681, 82.05, 82.08, 82.09; 436/50, 164, 165, 171; 235/468; 250/574–576

[56] References Cited

U.S. PATENT DOCUMENTS

| | | |
|---|---|---|
| 4,935,875 | 6/1990 | Shah et al. . |
| 5,305,093 | 4/1994 | Dosmann . |
| 5,385,847 | 1/1995 | Yip et al. . |
| 5,386,287 | 1/1995 | Berssen et al. . |
| 5,526,121 | 6/1996 | Sandifier et al. . |
| 5,646,736 | 7/1997 | Rampy et al. . |

*Primary Examiner*—K. Hantis
*Attorney, Agent, or Firm*—Jerome L. Jeffers

[57] ABSTRACT

A system for normalizing measurements obtained from spectrometers to correct for measurement biases in individual spectrometers. The normalization system is adapted for use in spectrometers having an optical assembly for obtaining characteristic data from a test sample. A normalization factor is obtained in each spectrometer by placing a holographic dispersion filter between the light source and detector in the position normally occupied by the test sample, the filter having been encoded with a symbol representing a nominal value of light expected to pass through the filter. The spectrometer determines the value of light passing through the filter and calculates a normalization factor based on the ratio between the nominal value of the filter and the actual value obtained by the spectrometer. The normalization factor is stored in system memory and the filter removed so that the spectrometer may thereafter be used to evaluate a plurality of test samples. The measured results obtained from the test samples are normalized by multiplying them by the stored normalization factor. Where measurements are obtained from a plurality of spectrometers, the normalized results vary less than about 10% from instrument to instrument for a variety of types of characteristic data, including turbidimetric microalbumin assays.

22 Claims, 3 Drawing Sheets

SPECTROMETER NORMALIZATION SYSTEM

FIELD OF THE INVENTION

The present invention relates generally to spectrometers for obtaining characteristic data from a test sample and, more particularly, to a system for normalizing measurements obtained from different spectrometers to account for measurement biases between individual spectrometers.

BACKGROUND OF THE INVENTION

Spectrometers are commonly used to obtain characteristic data from test samples such as, for example, blood, urine or other biological matter combined with other test components in an assay. The characteristic data may be obtained by means of colorimetric and/or turbidimetric measurements of the test sample. Briefly, colorimetric measurements evaluate the test sample through analysis of the particular color of the test sample, while turbidimetric measurements use a scattered light procedure to evaluate the concentration of particles suspended in the test sample. In a turbidimetric analysis, the particles are typically introduced in the test sample by an "agglutination" technique in which, for example, antibodies are bound to a particular protein or bound to a water suspensible particle (e.g., polystyrene or other latex) and protein.

There are several types of spectrometers known in the art which may be used to obtain characteristic data from a test sample. One type of spectrometer which may be used to obtain both calorimetric and turbidimetric measurements is a dual-beam spectrometer including a light source from which emanates a sample light beam in parallel with a reference light beam. A sample cartridge containing a test sample is mounted in the spectrometer housing in the path of the sample light beam but spaced apart from the reference light beam. Photodetectors aligned with the sample light beam and reference light beam detect the amount of light passing through the test sample and air, respectively, to perform turbidimetric and colorimetric measurements of the test sample.

In performing either colorimetric or turbidimetric analyses of a test sample, measurement errors may occur as a result of even slight misalignment of the optomechanical assembly (e.g. light beams and photodetectors) of the spectrometer. These errors are most pronounced in turbidimetric measurements, where it has been determined that accuracy errors increase exponentially in relation to the degree of optomechanical misalignment in the spectrometer. Typically, in any given instrument, accuracy errors caused by misalignment will result in a consistent "bias" unique to that instrument. Where multiple instruments are employed in the field, colorimetric or turbidimetric data obtained from the instruments will thereby vary as a result of the individual biases of each instrument, even when evaluating the same sample. Although a certain amount of such variations are tolerable, it is preferred that they be limited to a level of less than about 10 percent from one instrument to the next.

It is known in the art that such variations may be reduced to an acceptable level in the manufacturing process, through precise alignment of the opticomechanical components of each instrument. However, this method is impractical if correction is needed in a large number of instruments, especially where many of those instruments have already been delivered to the field. Another approach is to calibrate each instrument using samples of known turbidity. However, this approach is similarly impractical when correcting for biases between a large number of instruments, because it requires a correspondingly large number of samples of known turbidity, each of which must be accurately and precisely delivered to the customer in stable form.

In view of the above problems, there is a need for a system which reduces instrument-to-instrument variations in characteristic measurements obtained from spectrometers. The system should correct for optomechanical biases between a large number of spectrometers in the field without requiring realignment or reconstruction of their optical assemblies. The system should enable operators to correct biases in their individual instruments without any special training. The present invention is directed to addressing each of the aforementioned needs.

SUMMARY OF THE INVENTION

In accordance with one aspect of the present invention, there is provided a normalization system for a spectrometer having an optical assembly for obtaining characteristic data from a test sample. The optical assembly comprises a light source in optical alignment with a detector. When a test sample is positioned between the light source and detector, the light source directs a light beam through the test sample so that at least a portion of the light beam is measured by the detector, defining an actual value of characteristic data associated with the test sample. The normalization system is designed to convert the actual value to a normalized value such that the normalized value obtained by any individual spectrometer will vary no more than about 10% from the normalized value obtained from other spectrometers in the field. A normalization factor is obtained by placing a holographic dispersion filter between the light source and detector in the position normally occupied by the test sample, the filter having been encoded with a symbol representing a nominal value of light expected to pass through the filter. The spectrometer determines the value of light passing through the filter and calculates a normalization factor based on the ratio between the nominal value of the filter and the actual value obtained by the spectrometer. The normalization factor may be stored in system memory and the filter removed so that the spectrometer may be used to evaluate test samples. Measurements obtained from the test samples are normalized by multiplying them by the normalization factor associated with the spectrometer.

BRIEF DESCRIPTION OF THE DRAWINGS

The foregoing and other advantages of the invention will become apparent upon reading the following detailed description and upon reference to the drawings in which.

Figure 1:
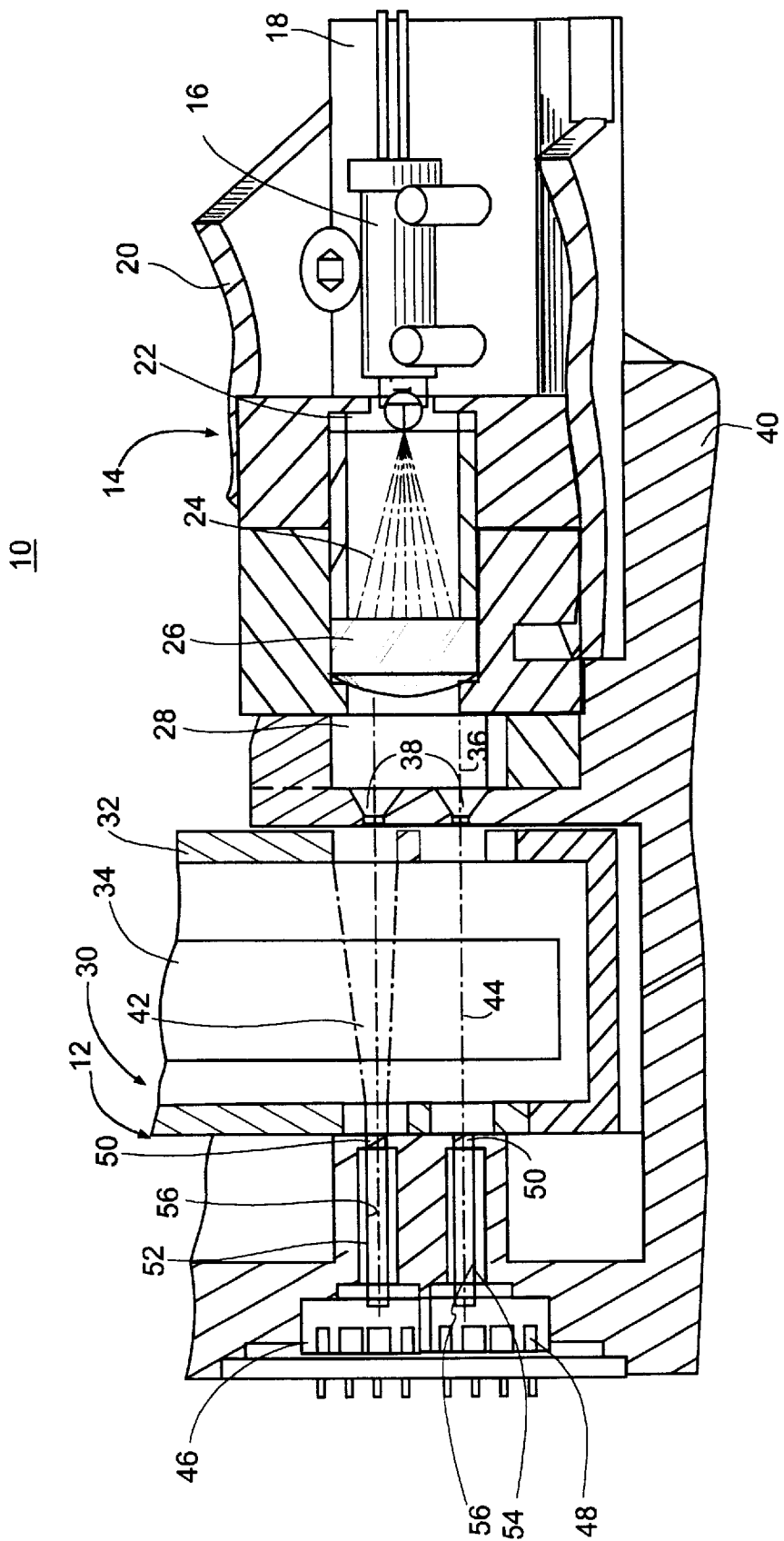
FIG. 1 is a side view of a prior art dual-beam spectrometer, partially in section, which may be used to obtain characteristic data from a test sample to be normalized according to principles of the present invention.

While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications. equivalents, and alternatives falling within the spirit and scope of the invention as defined by the appended claims.

DESCRIPTION OF SPECIFIC EMBODIMENTS

Turning now to the drawings and referring initially to FIG. 1, there is shown a prior art dual-beam spectrometer, designated generally by reference numeral 10, which may be used to obtain characteristic data of a test sample according to one embodiment of the present invention. It will be appreciated, however, that the spectrometer 10 shown in FIG. 1 is exemplary only. The present invention may be implemented with virtually any type of spectrometer using an optical assembly to obtain characteristic data from a test sample. At any rate, the spectrometer 10 shown in FIG. 1 is preferred because it is capable of performing high accuracy regular transmission turbidimetric measurements and high accuracy colorimetric measurements using the same optical system.

The spectrometer 10 includes an optical assembly generally comprising detection optics 12 in optical alignment with source optics 14. The source optics 14 produce a light beam which is detected by the detection optics 12. A test sample is typically positioned between the source optics 14 and detection optics 12 such that the light beam passes through the test sample before being detected by the detection optics 12. In turbidimetric measurements (i.e., where the sample is cloudy due to the presence of particles suspended in the sample), a portion of the incident light is scattered by the particles and the remaining portion is transmitted through the sample to the detection optics 12. The amount of light detected by the detection optics 12 thereby corresponds to the degree of turbidity of the sample, which in turn typically corresponds to the amount of protein or other material which is desired to be measured in the sample.

The source optics 14 include a lamp 16 mounted in a lamp holder 18. The lamp 16 preferably comprises a halogen light source, but it will be appreciated that the lamp 16 may comprise any suitable alternative light source known in the art. The lamp 16 has a frosted flame formed lens. The frost breaks up the image of the filament while still allowing the output to be condensed by the lens. A collimated spatial filter 22 is mounted adjacent to the lamp 16 to filter the light emanating from the lamp 16. A filtered beam of light 24 impinges on and passes through a collimation lens 26, then is directed onto a spectral bandpass filter 28. The lamp 16, spatial filter 22 and collimating lens 26 form a simple optical collimator that collimates light before it enters the bandpass filter 28. The amount of collimation can be measured by calculating the percentage increase in light beam diameter compared to the nominal or perfect collimated beam diameter at a detector plane. The collimation is directly proportional to the diameter of the collimation spatial filter 22. As the diameter of the filter 22 increases, the beam collimation degrades but the signal increases at the detector optics 12.

A sample area, generally designated by reference numeral 30, is provided for holding a sample to be measured by the spectrometer 10. Specifically, the sample area 30 includes a cartridge holder 32 mounted in the spectrometer housing 20 which is designed to hold a sample cartridge 34 containing a test sample. An example of a sample cartridge which may be used with the spectrometer 10 is provided in U.S. Pat. No. 5,385,847, incorporated herein by reference. A monochromatic beam 36 having a wavelength of 531 nm (nanometers) passes into source exit apertures 38 formed within an optics holder 40. The source exit apertures 38 form the monochromatic beam of light 36 into a sample light beam 42 and a reference light beam 44. In this arrangement, the sample light beam 42 passes through the sample contained in the sample cartridge 34 and the reference beam 44 passes under the sample cartridge 44 through the air.

The sample beam 42 is detected by a first detector/amplifier 46 and the reference beam 44 is detected by a second detector/amplifier 48. In one embodiment, the detectors 46 and 48 comprise Texas Instruments model no. 28934P photodetectors, but it will be appreciated that the photodetectors may comprise any suitable type known in the art. The first detector 46 is mounted within the optics holder 40 in a position perpendicular to the sample light beam 42. Similarly, the second detector 48 is mounted in the optics holder 40 in a position perpendicular to the reference light beam 44. To reach the first detector 46, the sample light beam 42 passes through a detection aperture 50. To minimize accuracy errors, the mechanical alignment between the source exit apertures 38 and the detection apertures 50 must be held to a close tolerance. The alignment is facilitated by means of the unibody molded optics holder 40 containing both the source exit apertures 38 and the detection apertures 50. Although turbidimetric accuracy errors increase exponentially with mechanical misalignment between the light source 16, the sample cartridge 34 and the light detection optics 12, these accuracy errors are minimized by the one-piece construction of the unibody molded optics holder 40, which maintains the source exit apertures 38 and the detection apertures 50 in a fixed relationship. Accuracy errors are further reduced by maintaining close manufacturing tolerances during the molding process of the optics holder 40.

Where turbidimetric measurements are concerned, spectrometers will preferably provide reliable transmission resolution between samples of high turbidity by detecting primarily the transmitted component of light (e.g., passing directly through the test sample) and rejecting the scattered or diffuse components of light. In the spectrometer 10 shown in FIG. 1, this is accomplished by means of a sample light beam detection aperture tube 52 and a reference beam detection aperture tube 54. The detection aperture tubes 52 and 54 comprise black ABS tubes that are mounted in the optics holder 40 between the sample cartridge 34 and the detectors 46 and 48, respectively. Each of the detection aperture tubes 52 and 54 has a length of 0.600 inch (1.52 cm) with $\frac{1}{40}$ internally threaded black walls. The inside diameter of each of the tubes 52 and 54 is 0.065 inch (0.165 cm). The threads 56 baffle a majority of the off axes light (diffuse component) that is present when measuring turbid samples.

The combination of the length and diameter of the detection aperture tubes 52 and 54 results in a detector viewing area that is limited to the sample area. Scattered light entering the tubes 52 and 54 from angles exceeding 5 degrees is prevented from passing down tubes 52 and 54 to the respective detectors 46 and 48. The resulting increase in relative absorbance of highly agglutinated samples provides increased absorbance resolution which is a contributing factor to the accuracy of the spectrometer 10.

As described briefly above, the spectrometer 10 may be used to obtain medical diagnostic data from test samples such as blood, urine or other biological matter. For example, as is known in the art, the spectrometer 10 may be used to evaluate a urine sample by measuring a urinary protein such as human serum albumin (microalbumin) turbidimetrically and the creatinine colorimetrically. This procedure is described in detail in U.S. Pat. No. 5,385,847, assigned to the assignee of the present invention and incorporated herein by reference. As described in the '847 patent, one of the purposes of measuring microalbumin levels in urine is to detect "microalbuminuria", characterized by an excessive amount of microalbumin in urine which, if uncorrected, may lead to a variety of kidney diseases. In patients with high urine flow rates, the amount of protein in the urine sample may be artificially lowered due to dilution of the urine sample. To correct for this problem, creatinine levels are typically measured to indicate the amount of dilution in the sample, then the measured protein level is normalized by taking the ratio of the protein level to the creatinine level. The common practice in present day clinical laboratories is to run the protein and creatinine assays separately, then combine the values obtained from these assays to generate the protein-creatinine ratio.

To determine the protein concentration turbidimetrically, turbidity is generated by introducing an antibody reagent into the urine sample. The antibody reagent reacts with the protein to produce an amount of agglutination products corresponding to the concentration of protein in the sample which can be measured by the spectrometer 10 or suitable equivalent. Alternatively, as is known in the art, the agglutination assay may be of the latex bound antibody type where an antibody, or fragment thereof, specific for particular epitopes of the protein, is bound to a water suspensible particle (e.g., polystyrene or other latex) and protein. By combining a large number of epitopic binding sites for the antibodies or antibody-latex and the plurality of epitopes on the protein, a large aggregate can be formed between the antibodies or antibody-latex and the protein. This aggregate creates the turbidity which can be measured by the spectrometer.

To determine the creatinine level colorimetrically. an alkaline reagent and creatinine indicator are introduced into the test sample to generate color which may be measured spectrophotometrically. For example. in a method known as the Jaffe method. a red-yellowish brown response is created in the test sample by the reaction of picric acid and creatinine in an alkaline solution. Alternatively, in a method known as the Benedict-Behre method, a colored response is created in the test sample by the reaction of 3,5-dinitrobenzoic acid and creatinine in the alkaline solution. However, it will be appreciated that any method may be used which produces a colored response when reacting with creatinine.

In analyzing a test sample using spectrophotometry, it is generally expected that the results obtained from any individual spectrometer will vary somewhat from the results obtained from other spectrometers in the field. Although a certain amount of such variations are acceptable, it is preferred that such variations be limited to about 10 percent or less from instrument to instrument. Typically, such variations are most pronounced when performing turbidimetric measurements of test samples, especially where the aggregate particle sizes associated with the test sample are relatively large. For example, turbidimetric microalbumin measurements (having particle sizes ranging between about 1100 nm to 100,000 nm) may vary up to 25% from instrument to instrument. Similarly, turbidimetric measurements of hemoglobin Hb $Al_c$ assays (having particle sizes of about 169 to 486 nm) may vary up to about 12% from instrument to instrument. In contrast, calorimetric measurements, such as a measurement of creatinine in a test sample, typically vary less than 10% from instrument to instrument. In either case, these variations may be partially attributed to slight variations in the optomechanical alignment of each instrument, creating a constant "bias" in each instrument which generally differs from the biases of other instruments in the field. One of the aspects of the present invention is to reduce these variations to an acceptable level by "normalizing" the results obtained from each individual instrument.

According to principles of the present invention, the normalization of any particular instrument may be accomplished by an operator simply placing a holographic dispersion filter (not shown) in the optical path of the spectrometer 10. The filter is packaged in a filter holder which fits within the cartridge holder 32 of the spectrometer 10 in the same manner as the sample cartridges to be evaluated. Preferably, the holographic dispersion filter comprises a 20° circular Light Shaping Diffuser™ (LSD) filter sold commercially by the Physical Optics Corporation of Torrance, Calif. The 20° LSD filter was found to be the best available filter for correction of albumin bias. In one embodiment of the present invention, the filter is assigned a "nominal" value corresponding to the amount of light expected to pass through the filter in a "nominal" spectrometer. Because the optical transmission properties of any particular filter will generally differ from that of other filters, each individual filter will typically have a nominal value unique from that of other filters.

The "nominal" spectrometer comprises an instrument or instruments known to have little or no optomechanical bias, or otherwise having a bias which falls close to the mean of all other instruments in the field. The assignment of nominal values for each individual filter is accomplished by placing the filter in the optical path of the nominal spectrometer and measuring the amount of light transmitted through the filter and detected by the nominal spectrometer. In one embodiment, the nominal value assigned to each filter comprises a numerical value corresponding to the amount of light absorbed by the filter. After a nominal value has been assigned by the nominal spectrometer(s), the nominal value may be verified by additional nominal spectrometer(s). The nominal value may be encoded on the filter or filter holder, for example, in the form of a bar code, numerical code or other suitable means known in the art.

When the filter is placed in the cartridge holder 32 of any individual instrument, a microprocessor (not shown) detects the presence of the filter and ascertains the nominal value associated with the filter, e.g., by reading the bar code on the filter. The microprocessor, which may be integral with or remote from the spectrometer 10, executes control software which controls operation of the spectrometer and evaluation of the filter. Evaluation of the filter is accomplished by placing the filter in the optical path of any individual instrument and measuring the amount of light transmitted through the filter and detected by the instrument. A correction, or normalization factor is calculated by the microprocessor based on the ratio of the nominal value of the filter and the amount of light detected by the individual instrument. The microprocessor stores the normalization factor in memory, and the filter can thereafter be removed from the spectrometer 10 and either discarded or inserted into any other spectrometer requiring normalization.

In performing subsequent evaluation of test samples, the microprocessor automatically converts the "actual" measured values associated with the test samples to normalized values by multiplying the actual values by the normalization factor stored in memory. Preferably, the entire process, from detection of the filter to normalization of the actual values, is automated so that the normalization process may be accomplished by the operator simply placing the filter in the cartridge holder 32 in the position normally occupied by a test sample. The normalization procedure may thereby be accomplished by operators having no special training. In one embodiment of the present invention, the control software of the spectrometer 10 is designed to prevent or inhibit evaluation of test samples by the spectrometer 10 until after the normalization factor associated with the filter has been obtained by the microprocessor. This ensures that the results obtained by the spectrometer 10 in evaluating any test sample will comprise normalized values which will not unduly vary from instrument to instrument.

Figure 2A:
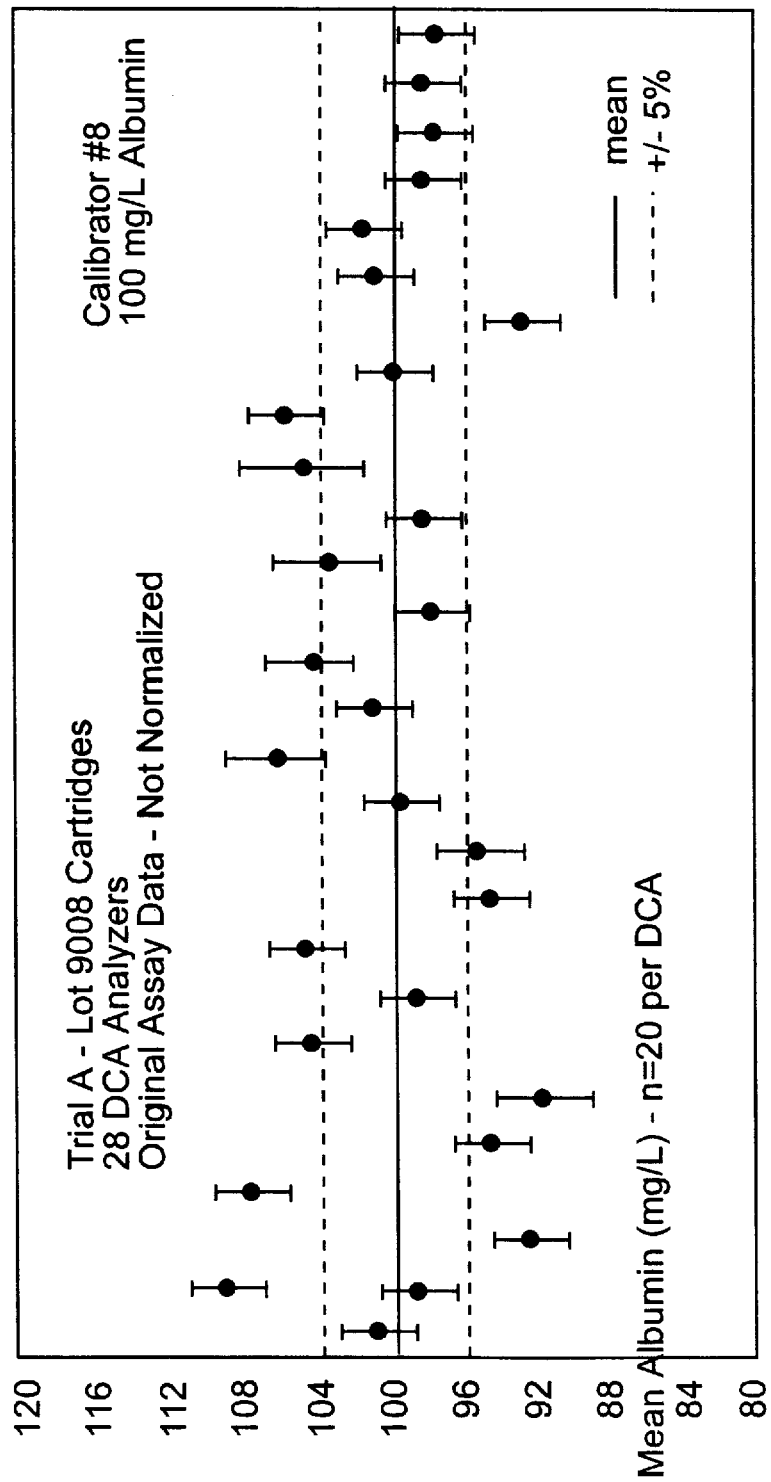
FIG. 2a is a plot of data obtained from turbidimetric microalbumin measurements in 28 unnormalized instruments.
Figure 2B:
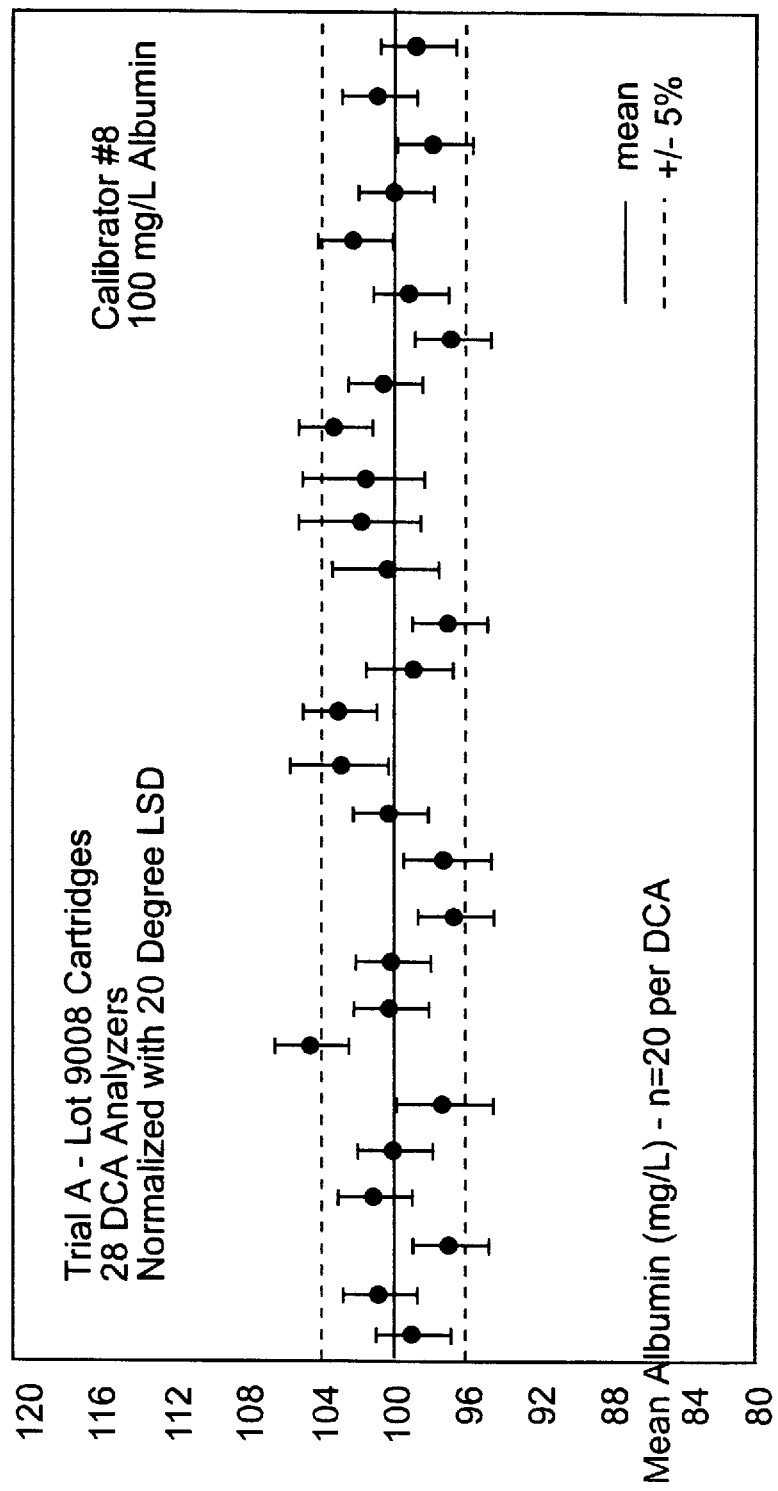
FIG. 2b is plot of data obtained from turbidimetric microalbumin measurements in 28 instruments which have been normalized according to principles of the present invention.

Experimentation has revealed that the above-described normalization procedure significantly reduces instrument-to-instrument variations in test sample measurements, including turbidimetric microalbumin assays. This improvement may be observed through comparison of FIG. 2a and 2b, which respectively plot data (with 1 SD error bars) obtained from a 100 mg/L microalbumin sample in 28 instruments before and after normalization. In FIG. 2a, the unnormalized albumin concentration results vary at about plus or minus 12% from the mean of all instruments, whereas in FIG. 2b, the normalized albumin concentration results are within about plus or minus 5% of the mean.

Bias spreads for the original and normalized albumin are presented in Table 1 below. Normalization with the 20° LSD filters significantly improved the biases for the albumin assay across the instruments tested.

TABLE 1

Instrument to Instrument Variability of the Albumin Assay

| Albumin | Bias spread | Within Instrument % C.V. | Between Instrument % C.V. | Overall % C.V. |
|---|---|---|---|---|
| Not Normalized: | | | | |
| 20 mg/L | 11.6% | 3.9% | 2.7% | 4.7% |
| 100 mg/L | 17.4% | 2.3% | 4.7% | 5.2% |
| 300 mg/L | 15.3% | 2.3% | 4.2% | 4.8% |
| Normalized: | | | | |
| 20 mg/L | 6.1% | 3.8% | 1.4% | 4.0% |
| 100 mg/L | 6.2% | 2.3% | 1.8% | 2.9% |
| 300 mg/L | 8.5% | 2.2% | 1.9% | 2.9% |

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. A normalization system for a spectrometer having an optical assembly for obtaining characteristic data from a test sample and a microprocessor for executing an initial software code in obtaining said characteristic data, said optical assembly comprising a light source in optical alignment with a detector, said test sample being removably positioned between said light source and said detector, said light source being adapted to direct a light beam through said test sample such that at least a portion of said light beam is measured by said detector defining an actual value of characteristic data obtained by said spectrometer corresponding to said test sample, said normalization system comprising:

a filter removably positioned between said light source and said detector in the same manner as said test sample, said filter having been encoded with a symbol representing a nominal value of light expected to pass through said filter, said light source being adapted to direct a light beam through said filter in the same manner as said test sample such that at least a portion of said light beam is measured by said detector defining a filter check value obtained by said spectrometer corresponding to said filter;

means associated with said microprocessor for reading said symbol and determining said nominal value, said microprocessor being adapted to divide said nominal value by said filter check value to define a normalization factor associated with said spectrometer; and means associated with said microprocessor for normalizing said actual value of characteristic data corresponding to said test sample by multiplying said actual value by said normalization factor.

2. The normalization system of claim 1 wherein said nominal value corresponds to the amount of light detected through said filter by a nominal spectrometer.

3. The normalization system of claim 1 wherein operation of said spectrometer is inhibited until said normalization factor is obtained by said microprocessor.

4. The normalization system of claim 1 wherein said symbol representing said nominal value comprises a bar code, said bar code being automatically read by said spectrometer in response to said filter being positioned between said light source and said detector in the same manner as said test sample.

5. The normalization system of claim 1 wherein said microprocessor includes a system memory for storing said normalization factor, said microprocessor being adapted to recall said normalization factor from said system memory to normalize a plurality of additional test samples.

6. A normalization system for a plurality of spectrometers each having an optical assembly for obtaining characteristic data from a test sample and a microprocessor for executing an initial software code in obtaining said characteristic data, each of said optical assemblies comprising a light source in optical alignment with a detector, said test sample being removably positioned between said light source and said detector in each of said spectrometers, said light source being adapted to direct a light beam through said test sample in each of said spectrometers such that at least a portion of said light beam is measured by said detector defining an actual value of characteristic data obtained by each respective spectrometer corresponding to the test sample being evaluated by each respective spectrometer, said normalization system comprising:

a plurality of filters each being removably positioned between said light source and said detector in respective ones of said spectrometers in the same manner as said test samples, each respective one of said filters having been encoded with a symbol representing a nominal value of light expected to pass through said filter, each spectrometer being adapted to direct a light beam through one of said filters in the same manner as said test sample such that at least a portion of said light beam is measured by said detector defining a filter check value obtained by each spectrometer corresponding to the filter used in each spectrometer;

means associated with said microprocessors for reading said symbol and determining said nominal value associated with said symbol in each of said spectrometers, each of said microprocessors automatically dividing said nominal value by said filter check value to define a normalization factor corresponding to each spectrometer; and means associated with said microprocessors for normalizing said actual values of characteristic data obtained by each respective spectrometer by multiplying said actual values by the normalization factor corresponding to each respective spectrometer.

7. The normalization system of claim 6 wherein said nominal value corresponds to the amount of light detected through said filter by a nominal spectrometer.

8. The normalization system of claim 6 wherein operation of each of said spectrometers is inhibited until said normalization factor is obtained by their respective microprocessors.

9. The normalization system of claim 6 wherein said symbol representing said nominal value in each respective filter comprises a bar code, each of said spectrometers automatically reading said bar code in response to one of said respective filters being positioned between said light source and said detector in the same manner as said test sample.

10. The normalization system of claim 6 wherein said microprocessor in each of said spectrometers includes a system memory for storing said normalization factor in each respective spectrometer, each microprocessor being adapted to recall said normalization factor from said system memory to normalize a plurality of additional test samples.

11. The normalization system of claim 6 wherein the test sample evaluated in a plurality of said spectrometers comprises a microalbumin assay and said characteristic data associated with said test samples comprises turbidimetric data, said normalized values of said characteristic data varying no more than about ten percent between individual ones of said plurality of spectrometers.

12. A normalization method for a spectrometer having an optical assembly for obtaining characteristic data from a test sample and a microprocessor for executing an initial software code in obtaining said characteristic data, said optical assembly comprising a light source in optical alignment with a detector, said test sample being removably positioned between said light source and said detector, said light source being adapted to direct a light beam through said test sample such that at least a portion of said light beam is measured by said detector defining an actual value of characteristic data obtained by said spectrometer corresponding to said test sample, said normalization method comprising the steps of:

removably positioning a filter between said light source and said detector in the same manner as said test sample, said filter having been encoded with a symbol representing a nominal value of light expected to pass through said filter;

directing a light beam through said filter in the same manner as said test sample such that at least a portion of said light beam is measured by said detector defining a filter check value obtained by said spectrometer corresponding to said filter;

determining said nominal value by reading said symbol;

dividing said nominal value by said filter check value to define a normalization factor associated with said spectrometer; and normalizing said actual value of characteristic data by multiplying said actual value by said normalization factor to define a normalized value of said characteristic data.

13. The normalization method of claim 12 wherein said nominal value corresponds to the amount of light detected through said filter by a nominal spectrometer.

14. The normalization method of claim 12 further comprising the step of inhibiting operation of said spectrometer until said normalization factor is obtained by said spectrometer.

15. The normalization method of claim 12 wherein said symbol representing said nominal value comprises a bar code, said step of determining said nominal value being accomplished automatically by said spectrometer in response to said filter being positioned between said light source and said detector in the same manner as said test sample.

16. The normalization method of claim 12 further comprising the steps of storing said normalization factor in system memory and periodically recalling said normalization factor from system memory, said step of recalling said normalization factor from system memory being accomplished prior to said step of normalizing said actual value of characteristic data.

17. A normalization method for a plurality of spectrometers each having an optical assembly for obtaining characteristic data from a test sample and a microprocessor for executing an initial software code in obtaining said characteristic data each of said optical assemblies comprising a light source in optical alignment with a detector, said test sample being removably positioned between said light source and said detector in each of said spectrometers, said light source being adapted to direct a light beam through said test sample in each of said spectrometers such that at least a portion of said light beam is measured by said detector defining an actual value of characteristic data obtained by each respective spectrometer corresponding to the test sample being evaluated by each respective spectrometer, said normalization method comprising:

removably positioning a filter between said light source and said detector in respective ones of said spectrometers in the same manner as said test samples, each filter having been encoded with a symbol representing a nominal value of light expected to pass through said filter;

directing a light beam through said filter in each of said spectrometers in the same manner as said test samples such that at least a portion of said light beam is measured by said detector defining a filter check value obtained by each spectrometer corresponding to the filter used in each spectrometer;

determining said nominal value by reading said symbol in each of said spectrometers;

dividing said nominal value by the filter check value in each of said spectrometers to define respective normalization factors associated with each of said spectrometers; and normalizing said actual values obtained by said spectrometers by multiplying said actual values by the respective normalization factors associated with each of said spectrometers.

18. The normalization method of claim 17 wherein said nominal value corresponds to the amount of light detected through said filter by a nominal spectrometer.

19. The normalization method of claim 17 further comprising the step of inhibiting operation of each respective spectrometer until said normalization factor is obtained by each respective spectrometer.

20. The normalization method of claim 17 wherein said symbol representing said nominal value in each respective filter comprises a bar code, said step of determining said nominal value being accomplished automatically by each respective spectrometer in response to one of said respective filters being positioned between said light source and said detector in the same manner as said test sample.

21. The normalization method of claim 17 further comprising the steps of storing said normalization factor in a system memory in each of said respective spectrometers and periodically recalling said normalization factor from said system memory in each of said respective spectrometers, said step of recalling said normalization factor from system memory being accomplished prior to said step of normalizing said actual value of characteristic data in each of said spectrometers.

22. The normalization method of claim 17 wherein said test samples evaluated in a plurality of said spectrometers comprises a microalbumin assay and said characteristic data associated with said test samples comprises turbidimetric data, said normalized values of said characteristic data varying no more than about ten percent between individual ones of said plurality of spectrometers.

* * * * *